US012636020B2

(12) United States Patent
Duquin et al.

(10) Patent No.: US 12,636,020 B2
(45) Date of Patent: May 26, 2026

(54) ANGLED PILOT HOLE ENTRY FOR ORTHOPEDIC GUIDE

(71) Applicant: Zimmer, Inc., Warsaw, IN (US)

(72) Inventors: Thomas R. Duquin, Warsaw, IN (US); Robert E Montgomery, Mishawaka, IN (US); Robert Douglas Krebs, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 249 days.

(21) Appl. No.: 18/486,706

(22) Filed: Oct. 13, 2023

(65) Prior Publication Data

US 2024/0122611 A1 Apr. 18, 2024

Related U.S. Application Data

(60) Provisional application No. 63/426,609, filed on Nov. 18, 2022, provisional application No. 63/416,101, filed on Oct. 14, 2022.

(51) Int. Cl.
*A61B 17/17* (2006.01)
*A61B 17/16* (2006.01)
(52) U.S. Cl.
CPC ................................. *A61B 17/1778* (2016.11)
(58) Field of Classification Search
CPC ............ A61B 17/1659; A61B 17/1684; A61B 17/1778
See application file for complete search history.

(56) References Cited

U.S. PATENT DOCUMENTS

| | | | |
|---|---|---|---|
| 7,883,513 B2 | 2/2011 | Ralph et al. | |
| 10,653,432 B2 | 5/2020 | Luttrell et al. | |
| 10,687,831 B2 | 6/2020 | Kovacs et al. | |
| 10,945,862 B2 | 3/2021 | Roby et al. | |
| 2013/0012945 A1 | 1/2013 | Chreene et al. | |
| 2014/0243828 A1 | 8/2014 | Heiney | |
| 2018/0333276 A1* | 11/2018 | Roby ................. A61B 17/1778 |
| 2022/0061860 A1 | 3/2022 | Daniel et al. | |

FOREIGN PATENT DOCUMENTS

| | | |
|---|---|---|
| DE | 102011079562 | 8/2018 |
| JP | 2025533229 | 10/2025 |
| WO | 2024081882 | 4/2024 |

OTHER PUBLICATIONS

"International Application Serial No. PCT US2023 076841, International Search Report mailed Feb. 6, 2024", 5 pgs.
"International Application Serial No. PCT US2023 076841, Written Opinion mailed Feb. 6, 2024", 5 pgs.

(Continued)

*Primary Examiner* — Samuel S Hanna
(74) *Attorney, Agent, or Firm* — SCHWEGMAN LUNDBERG & WOESSNER, P.A.

(57) ABSTRACT
A device may include a cutting instrument configured to cut a bone of a patient with one or more cutting features. A device may include a guide configured to mount to the bone, the guide defining an aperture having a guide hole portion and a pilot hole portion, wherein the pilot hole portion is configured to initially receive a portion of the bone cutting instrument, and wherein an axis of the pilot hole portion is oriented at an acute angle relative to an axis of the guide hole portion.

5 Claims, 12 Drawing Sheets

(56) References Cited

OTHER PUBLICATIONS

"International Application Serial No. PCT US2023 076841, International Preliminary Report on Patentability mailed Apr. 24, 2025", 7 pgs.

"European Application Serial No. 23805391.2, Response to Communication pursuant to Rules 1612 and 162 EPC filed Nov. 17, 2025", 20 pgs.

* cited by examiner

ANGLED PILOT HOLE ENTRY FOR ORTHOPEDIC GUIDE

CLAIM OF PRIORITY

This application claims the benefit of U.S. Provisional Patent Application Ser. No. 63/416,101, filed on Oct. 14, 2022, and also claims the benefit of U.S. Provisional Patent Application Ser. No. 63/426,609, filed on Nov. 18, 2022, the benefit of priority of which is claimed hereby, and each of which is incorporated by reference herein in its entirety.

FIELD OF THE DISCLOSURE

The present disclosure relates to orthopedic systems, methods and apparatuses including a guide for orienting a cutting device during an arthroplasty procedure.

BACKGROUND

In the human body, tissue can require repair. Such tissue includes bone, muscles, tendons, ligaments and cartilage. Forceful twisting, trauma or rotation of the knee, shoulder (or other joint) can tear or otherwise damage tissue. Disease can also necessitate replacement of bone(s) of the joint with one or more prosthetic components. Thus, a surgical repair of the tissue may be required in various circumstances.

Such replacement can require reaming or other cutting and preparation of bone. This repair can include guides to facilitate the cutting/preparation of the bone. Various guide assemblies have been developed for orienting bone cutting instruments and are generally effective for their intended purposes. Nevertheless, improved guides for facilitating cutting/preparation of the bone are still desirable.

In a healthy shoulder, the proximal humerus is generally ball-shaped, and articulates within a socket, called the glenoid, formed by the scapula to form the shoulder joint. Conventional implant systems for the total replacement of the shoulder joint due to disease or trauma, i.e., a total shoulder arthroplasty, generally replicate the natural anatomy of the shoulder, and typically include a humeral component having a stem which fits within the humeral canal, and an articulating head which articulates within the socket of a glenoid component implanted within the glenoid of the scapula.

Various types of shoulder implant systems are known including conventional or reverse joint replacement, revision shoulder arthroplasty and a partial (hemi) shoulder arthroplasty.

SUMMARY

The present disclosure provides orthopedic systems including a bone cutting device, driver, guide and other components. Disclosed systems, apparatuses and methods can be used for various purposes including joint repair and bone repair following a trauma.

The present inventors have realized that certain aspects of joint replacement procedures such as guiding a reamer to the glenoid during a shoulder replacement procedure can be overly complex and time consuming. This results from the patient's soft tissue interfering with the approach of the reamer to the guide. In particular, a guide hole of the guide is angled in an undesirable manner with respect to the soft tissue. As a result, surgeons must manipulate the soft tissue and insert the reamer against it to achieve the desired orientation for entry into the guide hole. Such manipulation can be undesirable as the process is time consuming, for example such as when requiring a greater exposure in the case of a posterior glenoid augmentation scenario, and can result in unnecessary trauma to the soft tissue.

The present inventors have recognized a guide with an angulated pilot hole relative to the guide hole. This angulated pilot hole allows the surgeon to have a more desirable approach for entry of the reamer into the guide thereby avoiding or reducing manipulation of the soft tissue. The angulated pilot hole can save time, can reduce surgical complexity and can reduce trauma to the soft tissue.

Further benefits are recognized by the present inventors and can include using the concept of a guide having an angled pilot hole relative to a guide hole for other procedures such as in a trauma procedure that wraps a suture or cable around or within a bone. Use of an angulated pilot hole such as disclosed herein can avoid stretching adjacent soft tissues. As an example, if a drill (or reamer with post) with a cannulation (for a secondary suture or cable to be introduced later through the cannula) was used with the angulated pilot hole techniques discussed herein, the approach angle could be increased dramatically, sparing surrounding soft tissues from excessive stretching during the procedure. The guide(s) disclosed can have a bottom/sides of the pilot hole shaped (e.g., provided with one or more surfaces with radii) to facilitate re-orientation of the cutting instrument from the pilot hole into the guide hole. Again, this configuration can save time and reduce surgical effort. Further benefits contemplated include the guide can be configured with an oval, oblong, or compound curved hole at a proximal surface of the guide to improve the entry angle and/or to better facilitate coupling of the guide with an inserter/removal tool.

The above discussion is intended to provide an overview of subject matter of the present patent application. It is not intended to provide an exclusive or exhaustive explanation of the invention. The description below is included to provide further information about the present patent application To better illustrate the apparatuses, systems and methods disclosed herein, a non-limiting list of examples and techniques is provided here:

Example 1, the techniques described herein relate to a system for performing an orthopedic surgical procedure, the system optionally including: a cutting instrument configured to cut a bone of a patient with one or more cutting features; a guide configured to mount to the bone, the guide defining an aperture having a guide hole portion and a pilot hole portion, wherein the pilot hole portion is configured to initially receive a portion of the bone cutting instrument, and wherein an axis of the pilot hole portion is oriented at an acute angle relative to an axis of the guide hole portion.

Example 2, the techniques described herein relate to a system, wherein the guide optionally has one or more reorientation surfaces that form the aperture, wherein the one or more reorientation surfaces are configured to reposition the cutting instrument to be received in the guide hole portion.

Example 3, the techniques described herein relate to a system, wherein optionally the one or more reorientation surfaces form one or more of a side and bottom of the pilot hole portion, and wherein the one or more reorientation surfaces include a radius of curvature.

Example 4, the techniques described herein relate to a system, wherein optionally the cutting instrument includes a peg distal of the one or more cutting features, wherein the peg is the portion of the bone cutting instrument initially received by the pilot hole portion, and wherein the peg has a blunt tip configured to engage the one or more reorientation surfaces.

Example 5, the techniques described herein relate to a system, wherein optionally the cutting instrument is rotatable within the pilot hole portion of the aperture and rotation of the cutting instrument contacts the peg with the one or more reorientation surfaces to reposition the peg to be received in the guide hole portion.

Example 6, the techniques described herein relate to a system, wherein optionally the one or more reorientation surfaces form a partial spherical shape.

Example 7, the techniques described herein relate to a system, wherein the guide optionally includes a proximal surface and the aperture communicates with the proximal surface at an opening, and wherein the opening in cross-section is one of oval, oblong or compound curved.

Example 8, the techniques described herein relate to a system, further optionally including an instrument configured to insert and/or remove the guide, wherein the guide includes a groove configured to be engaged by a prong of the instrument, and wherein the instrument includes a projection configured to insert into the aperture and engage a side surface of the aperture.

Example 9, the techniques described herein relate to a system, wherein the guide hole portion optionally includes a thru hole that extends to communicate with a distal surface of the guide.

Example 10, the techniques described herein relate to a guide for orienting a bone cutting apparatus to cut a bone during an orthopedic surgical procedure, the guide optionally including: a distal surface having one or more pegs configured to mount to the bone; and a body defining an aperture having a guide hole portion and a pilot hole portion, wherein the pilot hole portion has an axis that is orientated at an acute angle relative to an axis of the guide hole portion.

Example 11, the techniques described herein relate to a guide, wherein the guide optionally has one or more reorientation surfaces that form the aperture, wherein the one or more reorientation surfaces form one or more of a side and bottom of the pilot hole portion, and wherein the one or more reorientation surfaces include a radius of curvature.

Example 12, the techniques described herein relate to a guide, wherein optionally the one or more reorientation surfaces form a partial spherical shape.

Example 13, the techniques described herein relate to a guide, further optionally including a proximal surface of the guide, wherein the aperture communicates with the proximal surface at an opening, and wherein the opening in cross-section along the proximal surface is one of oval, oblong or compound curved in a cross-section.

Example 14, the techniques described herein relate to a guide, wherein the guide hole portion optionally includes a thru hole that extends to communicate with the distal surface.

Example 14, the techniques described herein relate to a method of cutting a bone during an orthopedic surgical procedure, the method optionally including: mounting a guide to the bone; providing a cutting instrument configured to cut the bone of a patient with one or more cutting features; initially inserting a portion of the cutting instrument into a pilot hole portion of an aperture of the guide; reorienting the cutting instrument with the portion inserted in the pilot hole portion such that the portion is received in a guide hole portion of the aperture; and operating the cutting instrument to cut the bone as guided by the guide hole portion of the aperture.

Example 16, the techniques described herein relate to a method, wherein optionally reorienting the cutting instrument with the portion inserted in the pilot hole portion such that the portion is received in the guide hole portion of the aperture includes contacting one or more surfaces that form the aperture to reposition the cutting instrument to be received in the guide hole portion.

Example 17, the techniques described herein relate to a method, wherein optionally the surfaces form one or more of a side and bottom of the pilot hole portion, and wherein the one or more surfaces include a radius of curvature.

Example 18, the techniques described herein relate to a method, further optionally including rotating the cutting instrument with the portion inserted in the pilot hole portion and contacting the one or more surfaces to reposition the portion of the cutting instrument to be received in the guide hole portion.

Example 19, the techniques described herein relate to a method, wherein optionally the one or more surfaces form a partial spherical shape.

Example 20, the techniques described herein relate to a method, wherein initially inserting the portion of the cutting instrument into the pilot hole portion of the aperture of the guide optionally includes passing the cutting instrument through an opening at a proximal surface of the guide, and wherein the opening in cross-section is one of oval, oblong or compound curved.

Example 21 is any one or combination of the techniques, apparatuses, systems and method examples above including any one or combination of the features disclosed herein.

BRIEF DESCRIPTION OF THE FIGURES

The above-mentioned and other features and advantages of this disclosure, and the manner of attaining them, will become more apparent and the disclosure itself will be better understood by reference to the following description of examples taken in conjunction with the accompanying drawings, wherein.

Corresponding reference characters indicate corresponding parts throughout the several views. The exemplifications set out herein illustrate examples of the disclosure, and such exemplifications are not to be construed as limiting the scope of the disclosure any manner.

DETAILED DESCRIPTION

In describing the examples of the disclosure illustrated and to be described with respect to the drawings, specific terminology will be used for the sake of clarity. However, the disclosure is not intended to be limited to any specific terms or illustrations used herein, and it is to be understood that each specific term includes all technical equivalents.

The present disclosure is directed to apparatuses, systems and methods that can be used in joint replacement and other orthopedic procedures that utilize guides to orient/guide a bone cutting instrument. The example description relates to apparatuses and systems used in a total or revision shoulder arthroplasty. However, the methods, apparatuses and systems can be used for other joints and/or in other procedures such as orthopedic bone stabilization after a trauma. It is contemplated that the apparatuses, systems, techniques and methods disclosed herein could be used with any applicable orthopedic procedure not just a total shoulder replacement procedure. Thus, the concepts of the present application are not limited by the examples provided herein. Similarly, the term "bone" as used herein is not limited to the glenoid but can include any applicable bone of the body.

Figure 1:
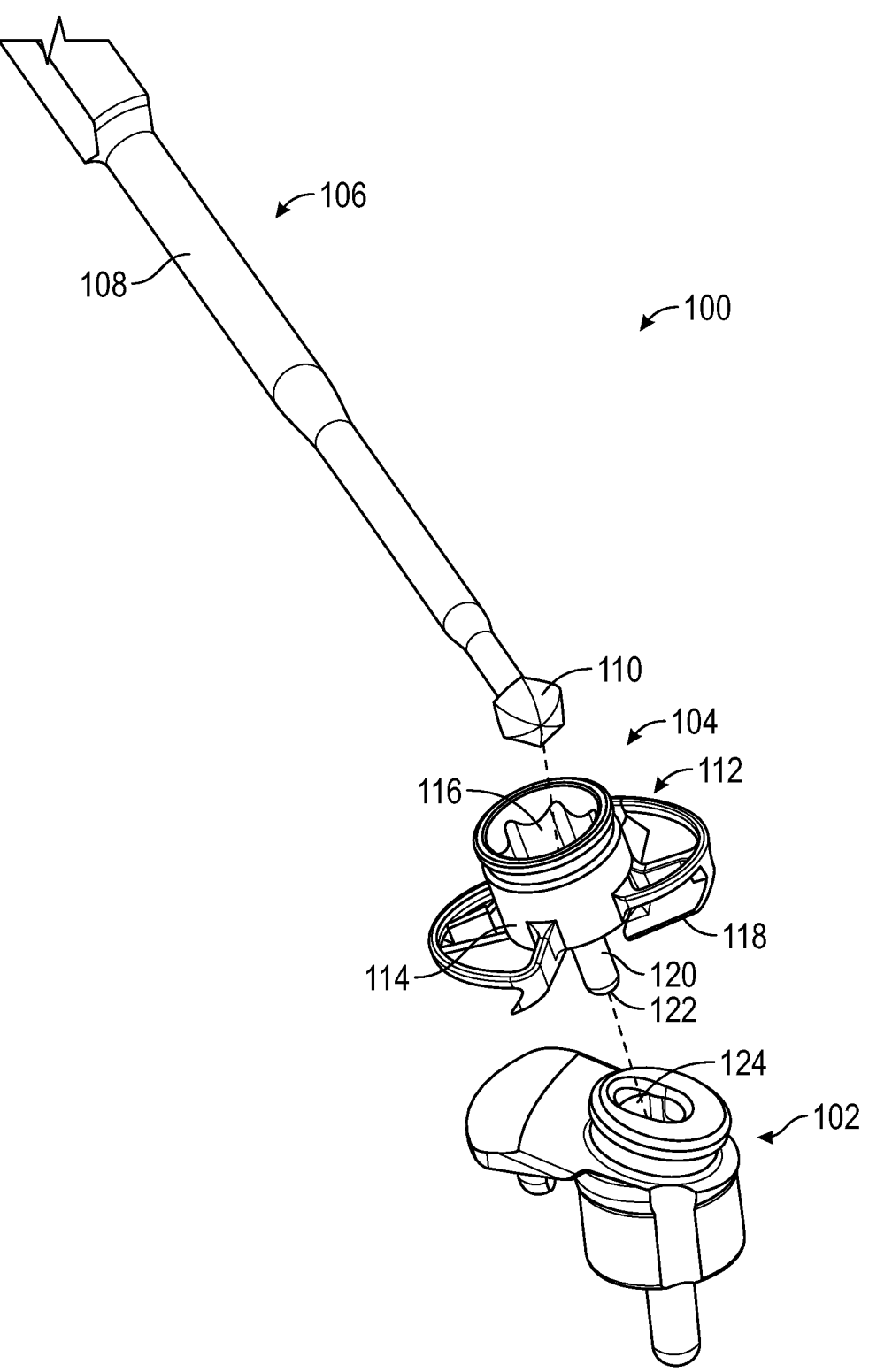
FIG. 1 is an exploded perspective view of a system for a shoulder replacement procedure including a drive tool, a cutting instrument and a guide according to an example of the present application.

FIG. 1 illustrates a system 100 that can include a guide 102, a cutting instrument 104 and a drive tool 106.

The drive tool 106 can comprise a reamer driver or other drive device as known in the art. Examples of such devices can be found in U.S. Pat. Nos. 10,687,831 and 10,945,862, the entire discloses of each of which are incorporated by reference in their entirety. The drive tool 106 can include a shaft 108 and a head 110. The head 110 can be configured as a gear, hex or other type coupling device, for example. Thus, the head 110 can have teeth or other features with planar, curved or beveled surfaces or the like. As shown in FIG. 1, the head 110 can be configured to mate/mesh with and drive a corresponding female component of the cutting instrument 104. Due to the coupling via the mating components, rotation of the drive tool 106 can be passed from the drive tool 106 to the cutting instrument 104.

The cutting instrument 104 can be a reamer 112 according to the example of FIG. 1. However, other types of cutting instruments such as broaches, drills, cannulated drills, needles, osteotomes, rongeurs, bone cutters, punches, etc. are also contemplated. The reamer 112 can include a main body 114 having a coupling feature 116, one or more cutting features 118 and a peg 120.

The coupling feature 116 can be part of the main body 114 on a proximal side thereof. The coupling feature 116 can be a female or male feature configured to receive or otherwise couple with the head 110 for rotation of the cutting instrument 104. The main body 114 can be generally cylindrical in construction and can be constructed of a metal, a polymer, a ceramic, or any combination thereof.

The one or more cutting features 118 can be coupled to and can extend outward around the main body 114. The one or more cutting features 118 (e.g., blades, barbs, teeth, sharps, etc.) can have a construction as known in the art and can be configured to cut and remove tissue (including soft tissue and bone) of a patient. In the example of FIG. 1, the one or more cutting features 118 can be configured (sized and shaped) to cut and remove the glenoid of the shoulder.

The peg 120 can extend from the main body 114 distally and can be positioned distal of the one or more cutting features 118. Thus, the peg 120 can be on an opposing side of the main body 114 from the coupling feature 116. The peg 120 can be configured as a boss or other feature to aid guided coupling of the cutting instrument 104 with the guide 102. Put another way, the peg 120 can be used with an aperture of the guide 102 to guide insertion of the cutting instrument 104 to the bone or soft tissue.

As shown in FIG. 1, the peg 120 can have a blunt tip 122. However, other tip geometries (conical, frustoconical, semi-spherical, sharp, etc.) are contemplated as known in the art. The peg 120 can be appropriately sized for insertion and capture in an aperture 124 of the guide 102 as further described herein. The aperture 124 is shown as a thru hole in FIG. 2 and can extend from a proximal side to a distal side of the guide 102. However, other configurations for the aperture 124 such as being a blind hole with a bottom or a thru hole extending to a medial or lateral side of the guide 102 are contemplated. The guide 102 can be constructed of a metal, a polymer, a ceramic, or any combination thereof. The shape of the guide 102 and other features thereof will be further discussed in reference to FIGS. 2-4C.

Figure 2:
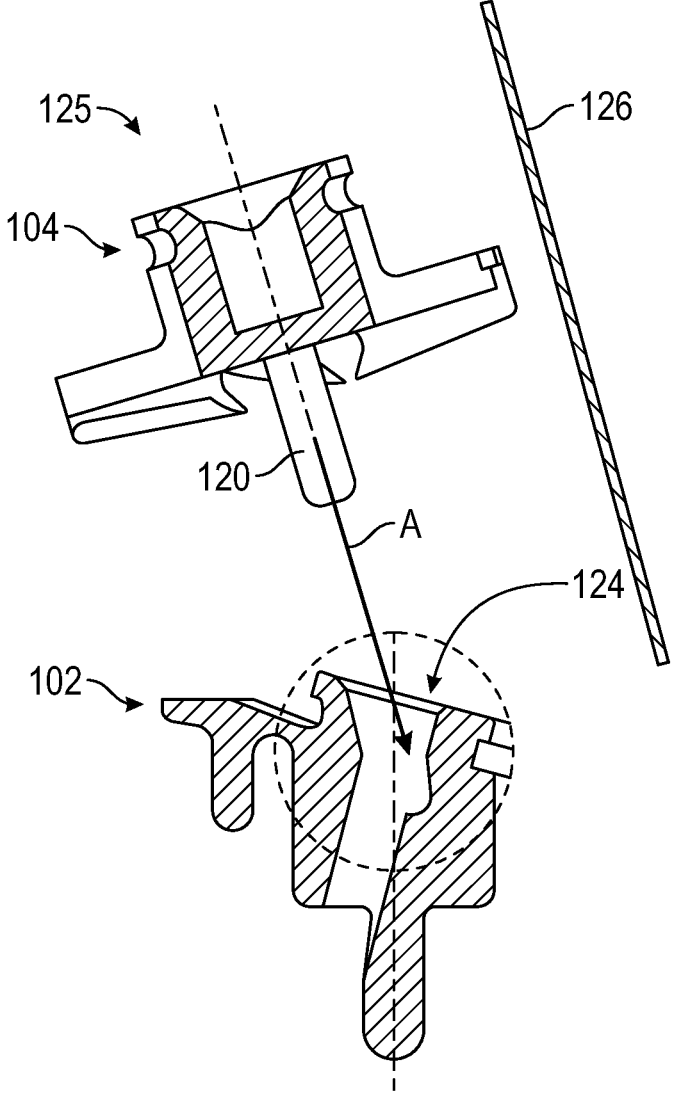
FIG. 2 shows cross-sectional view of the cutting instrument and the guide of FIG. 1 showing an approach of the cutting instrument at an angle to a guide hole portion facilitated by a pilot hole portion of an aperture according to an example of the present application.

FIG. 2 shows the cutting instrument 104 having an angle of approach toward the aperture 124 of the guide 102 that avoids or minimizes impact such as stretching/manipulation on soft tissue 126 of the shoulder joint 125. This angle of approach for the cutting instrument 104 can allow a portion of the cutting instrument 104 to be initially inserted into the aperture 124 (e.g., the peg 120 can be partially inserted down into the aperture 124) at an angle/tilt so as to avoid soft tissue 126 of the shoulder joint 125. The insertion of the cutting instrument 104 into the aperture 124 is shown by arrow A in FIG. 2.

Figure 3A:
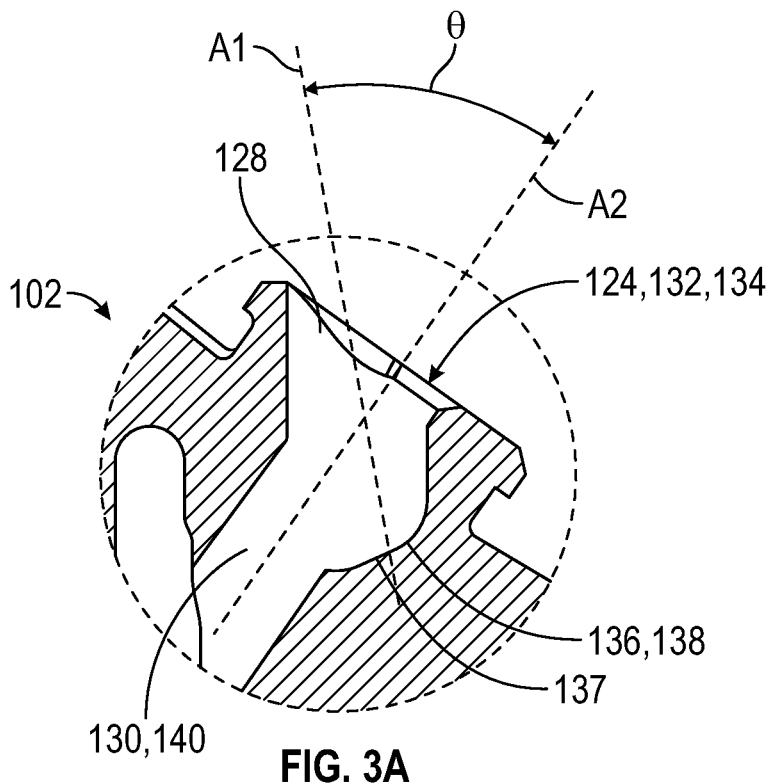
FIGS. 3A-3C show enlarged cross-sectional views of various sizes of the guide of FIGS. 1 and 2 showing the pilot hole portion and part of the guide hole portion of the aperture according to an example of the present application.
Figure 3B:
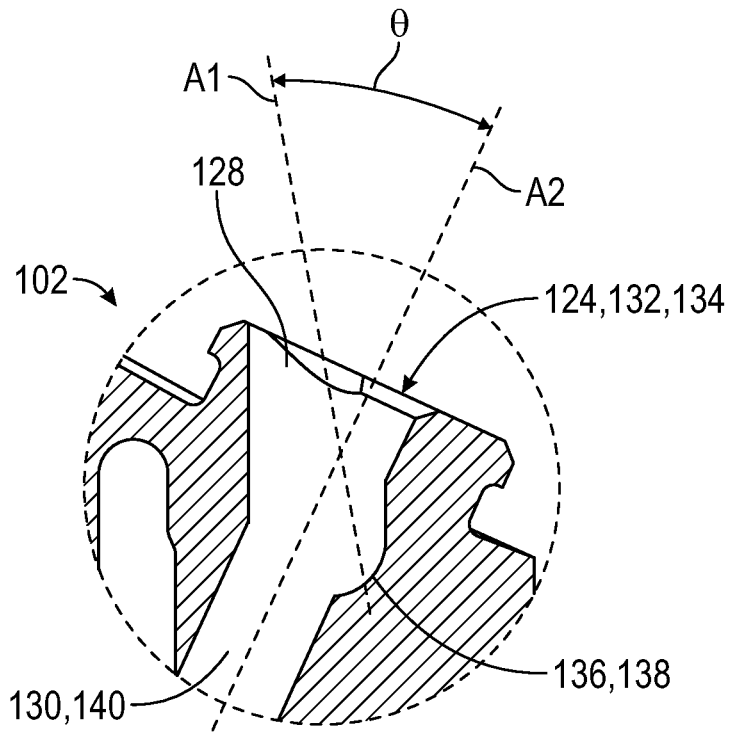
Figures 3C, 4:
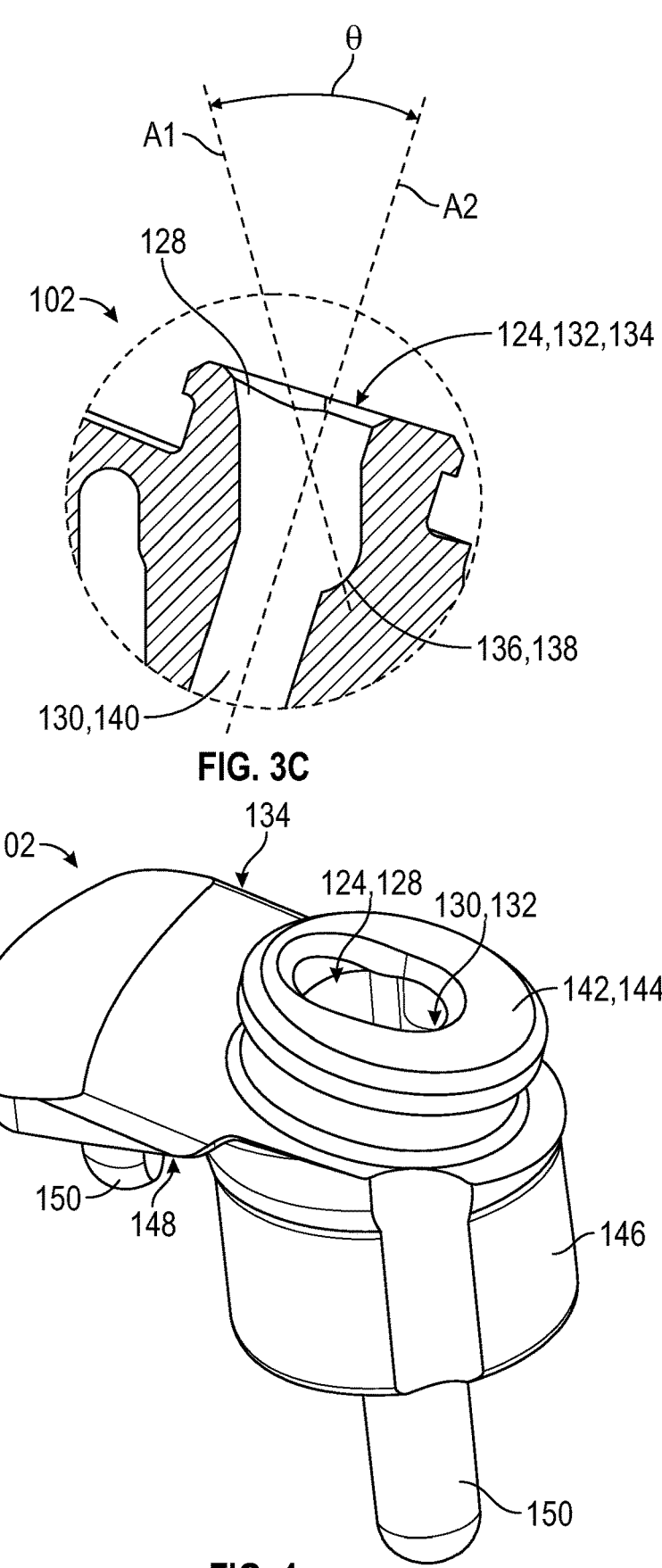
FIGS. 4, 4A, 4B, and 4C show views of the guide of FIGS. 1-3C from various perspectives according to another example of the present application.

The angle/tilt of the cutting instrument 104 and peg 120 of FIG. 2 (also sometimes called the angle of attack, approach angle, entry angle or insertion angle herein) can be determined by an angle $\theta$ of a pilot hole portion 128 of the guide 102 as shown in the enlarged cross-sectional views of FIGS. 3A-3C. In particular, the angle $\theta$ can be measured from an axis A1 of a pilot hole portion 128 of the aperture 124 relative to an axis A2 of a guide hole portion 130 of the aperture 124. FIGS. 3A-3C show three different standard sizes for the guide 102, a large (FIG. 3A), a medium (FIG. 3B) and a small (FIG. 3C). However, further sizes, shapes and orientations for the guide 102 and the features thereof including the pilot hole portion 128 and the guide hole portion 130 are contemplated.

FIGS. 3A-3C show the angle θ as measured from the axis A1 of the pilot hole portion 128 of the aperture 124 to the axis A2 of the guide hole portion 130. The angle θ can be an acute angle and can be between 45 degrees and 10 degrees, inclusive, for example. However, other degrees of angulation including oblique angulation as measured by the angle θ are contemplated.

The aperture 124 can have an opening 132 at a proximal side 134 of the guide 102. The pilot hole portion 128 and the guide hole portion 130 can communicate with one another. This allows for reorientation of the cutting instrument 104 (FIGS. 1 and 2) as further discussed herein. The pilot hole portion 128 can extend from one side of the axis A2 of the guide hole portion 130 to a second side thereof. The pilot hole portion 128 can be formed partially at a distal end and/or side by one or more surfaces 136 (sometimes called one or more reorientation surfaces herein). The one or more surfaces 136 can be located radially to a side of the axis A2 of the guide portion 130. Optionally, the one or more surfaces 136 can be curved (e.g., can have one or more radii 138). This curvature can provide for a partially spherical or another type of shape for the one or more surfaces 136. However, in some examples such as the large guide 102 of FIG. 3A, the one or more surfaces 136 can be otherwise shaped such as to have a flat (non-curved) region 137. Region 137 may be oriented at a right angle to the walls of the oblong shape or at an angle to the oblong shape walls (as depicted in FIG. 3A).

The one or more surfaces 136 can be a distal and/or side termination point for the pilot hole portion 128. Thus, the one or more surfaces 136 can be configured to act as an initial stop for the peg 120 (FIGS. 1 and 2) upon partial entry. Additionally, the one or more surfaces 136 can be shaped with the one or more radii 138 (or other shape) to redirect/reorient the peg 120 upon contact therewith into a distal part 140 of the guide hole portion 130. Such redirection/reorientation can alter the position of the cutting instrument 104 (FIGS. 1 and 2) as further discussed and illustrated herein.

The guide hole portion 130 can extend along the axis A2 for an entirety of the length thereof. The length (depth) of the guide hole portion 130 can be greater than that of the pilot hole portion 128. Pilot hole portion 128 can have a depth sufficient for only partial entry of the peg 120 (FIGS. 1 and 2), for example. In contrast, the depth of the guide hole portion 130 can be sufficient to receive substantially an entirety of the peg 120. Furthermore, the intent of the guide hole portion 130 is to provide a desired orientation and/or depth to the cutting instrument 104 for contacting and cutting tissue such as bone. Put another way, the configuration of the guide hole portion 130 can bring the cutting instrument 104 (FIGS. 1 and 2) into contact with the glenoid at a desired orientation and allow for removal of the glenoid to a desired depth such that implants can be subsequently added to the glenoid. In contrast, the configuration of the pilot hole portion 128 differs from the guide hole portion 130 and can be used only for entry to avoid or minimize contact of the cutting instrument 104 (FIGS. 1 and 2) with soft tissue as illustrated including in FIG. 2.

The depth of the pilot hole portion 128 as measured from the opening 132 to the one or more surfaces 136 can vary and can be between 0.20 inches and 0.45 inches, for example. However, other depths including those for other surgical applications are contemplated. The radius of the distal part 140 can be between 0.025 inches and 0.10 inches, for example. However, other sizes for the distal part 140 including for other surgical applications are contemplated. The size of the opening 132 can vary as further discussed herein. Optionally, the radius of the opening 132 can be between 0.05 inches and 0.30 inches.

Figure 4A:
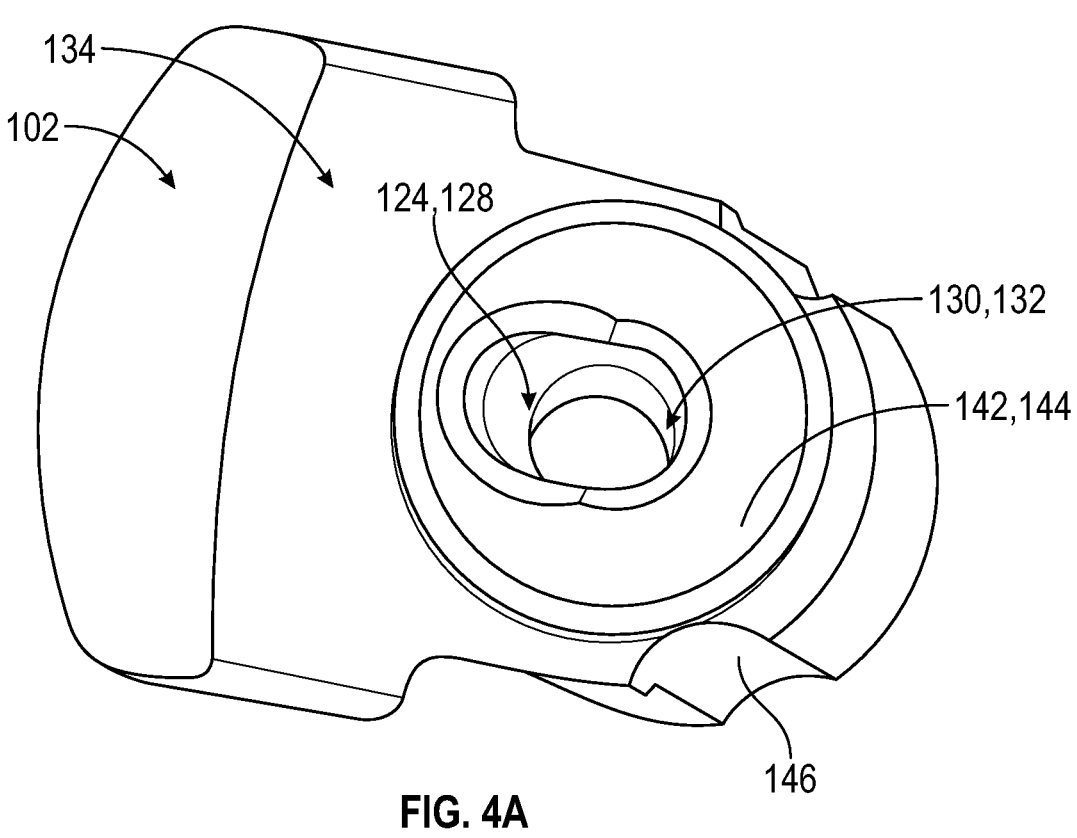
Figure 4B:
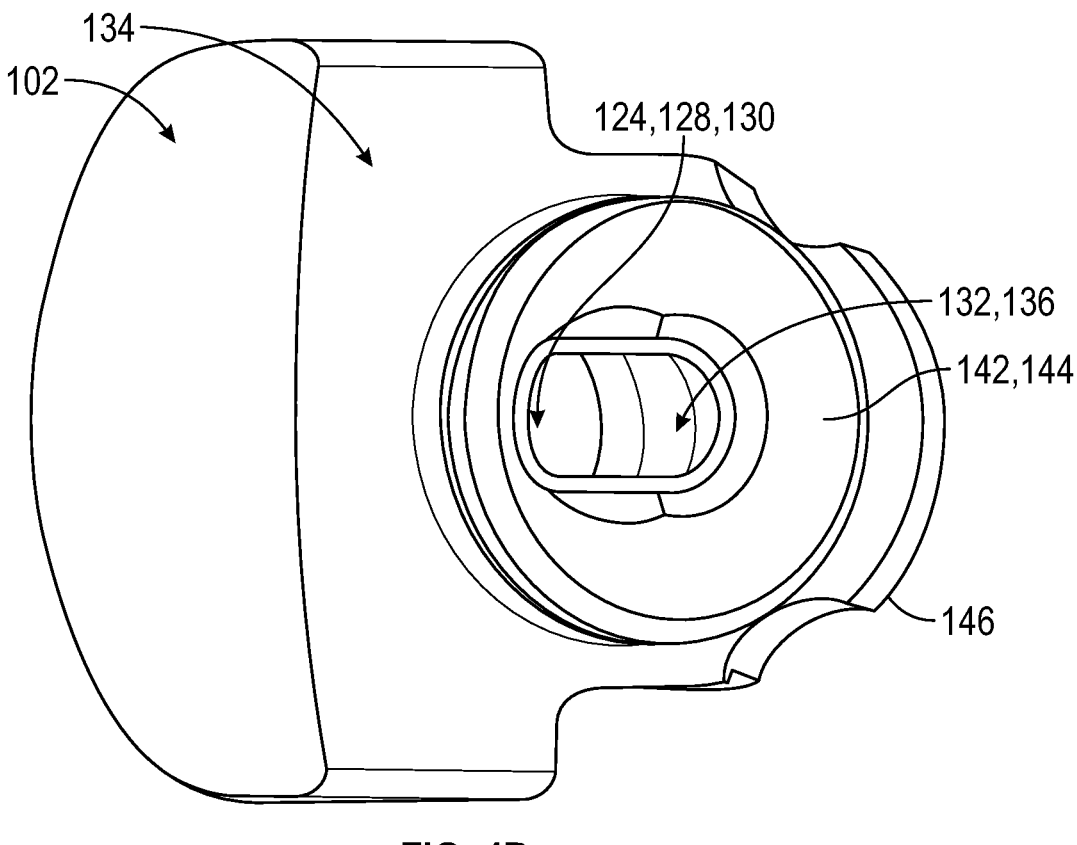

FIGS. 4, 4A, 4B, and 4C show the guide 102 from various perspectives. As shown in FIGS. 4, 4A and 4B the guide 102 can include the aperture 124 with the pilot hole portion 128 and the guide hole portion 130, the opening 132 and the proximal side 134. FIG. 4B also shows the one or more surfaces 136 within the aperture 124.

The proximal side 134 can be formed in part by a projection 142 that has the aperture 124 therein. The proximal side 134 can have a proximal surface 144. The projection 142 can extend from a main body 146 of the guide 102. As shown in FIGS. 4, 4A and 4B, the opening 132 can have a compound curvature at the proximal surface 144 and the proximal side 134. Chamfering of the guide 102 leading into the aperture 124 can be provided.

Figure 4C:
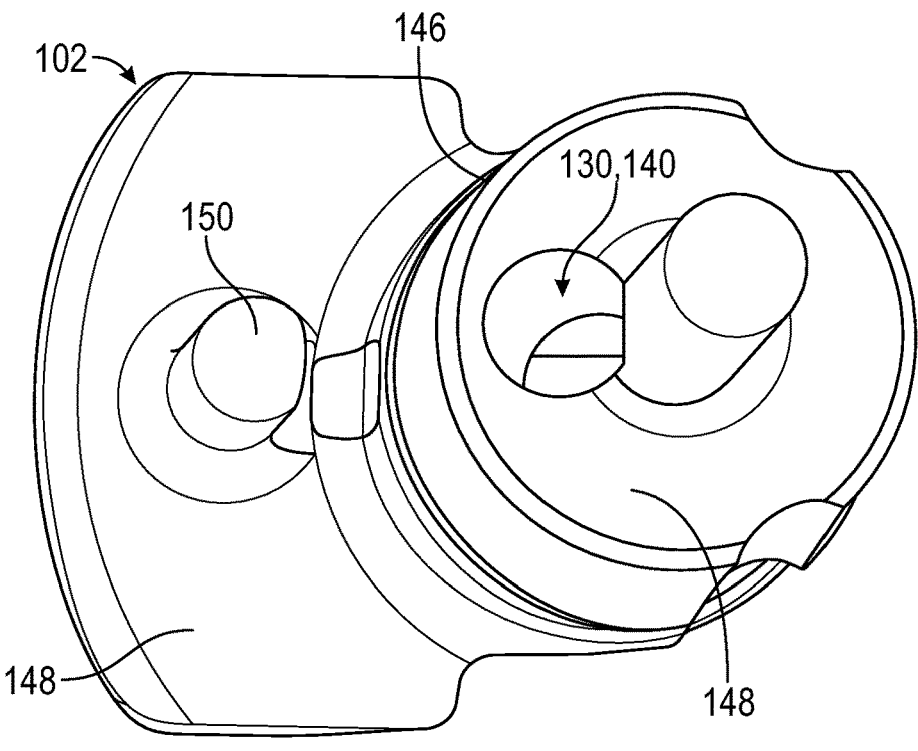

As shown in FIGS. 4 and 4C, the main body 146 can extend to a distal side 148 that opposes the proximal side 134. The distal side 148 can include one or more pegs 150 for fixation of the guide 102. As shown in FIG. 4C, the guide hole portion 130, and in particular the distal part 140 thereof can extend through the main body 146 to the distal side 148. Thus, the guide hole portion 130 can comprise a thru hole extending from the proximal side 134 entirely through the guide 102 to the distal side 148. As discussed previously, the guide hole portion 130 need not be a thru hole according to further examples.

Figure 5:
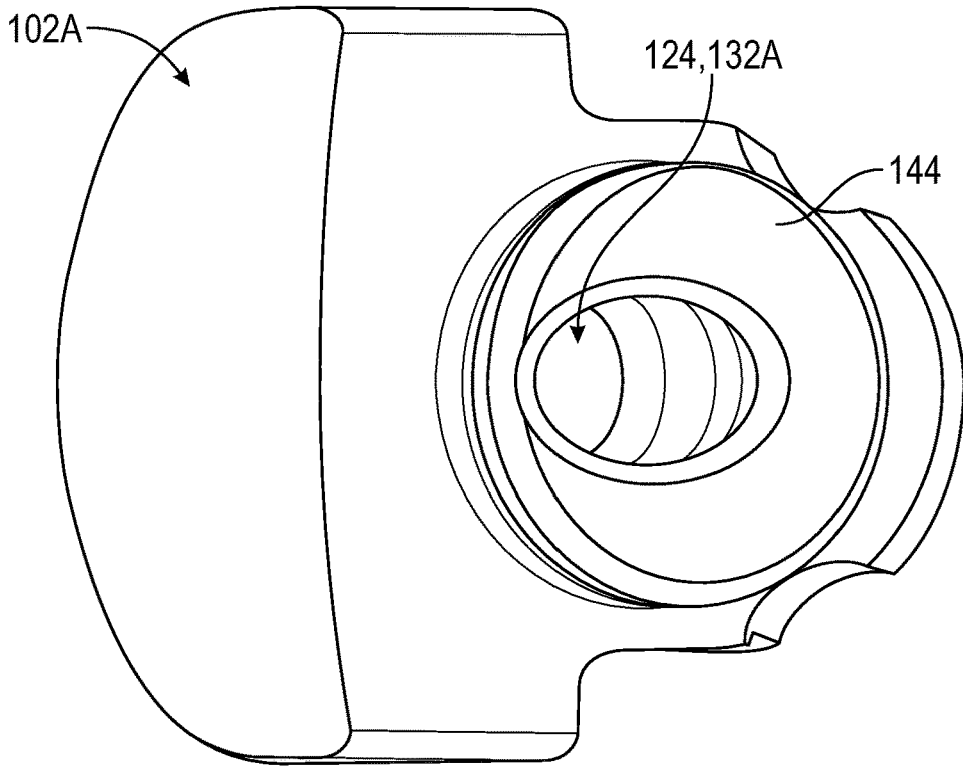
FIG. 5 is a perspective view of a proximal surface of another example guide having an oval shaped opening at the proximal surface for the aperture according to an example of the present application.

FIG. 5 shows a guide 102A with different construction from the guide 102 of FIGS. 1-4C. In particular, the guide 102A can have an opening 132A to the aperture 124 at the proximal surface 144 that is oval shaped rather than the compound curved shape previously shown.

Figure 6:
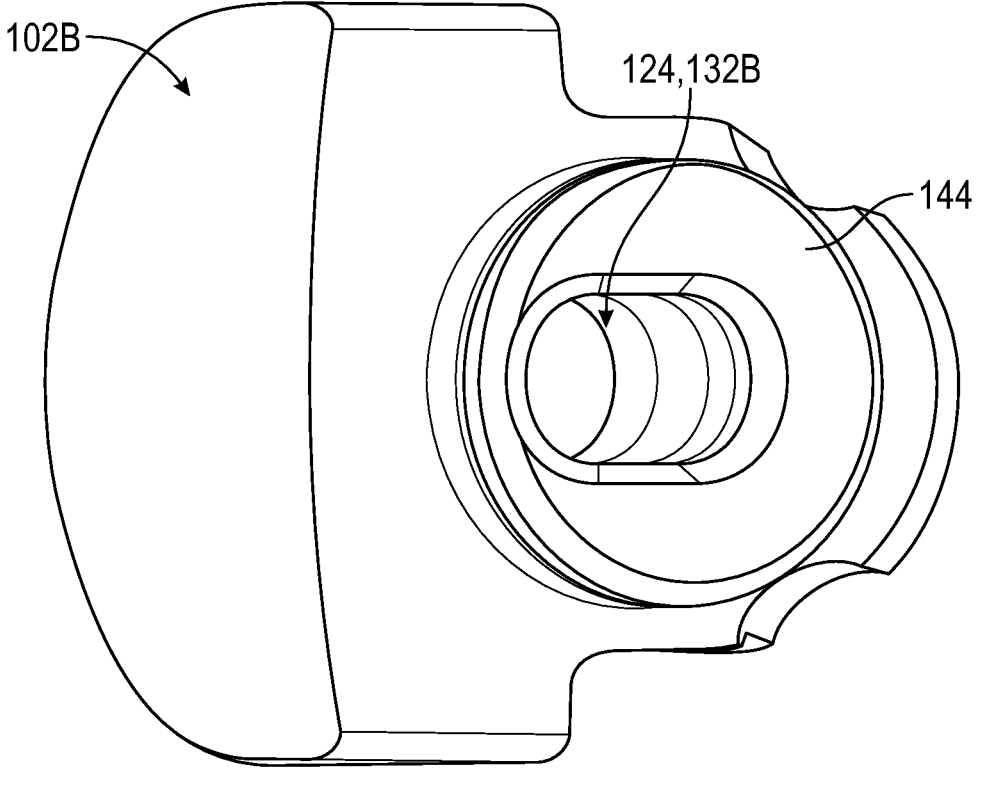
FIG. 6 is a perspective view of a proximal surface of another example guide having an oblong shaped opening at the proximal surface for the aperture according to an example of the present application.

Similarly, FIG. 6 shows a guide 102B of slightly different construction from the guide 102 of FIGS. 1-4C. In particular, the guide 102B can have an opening 132B to the aperture 124 at the proximal surface 144 that is oblong or slot shaped rather than the compound curved shape previously shown.

Figure 7:
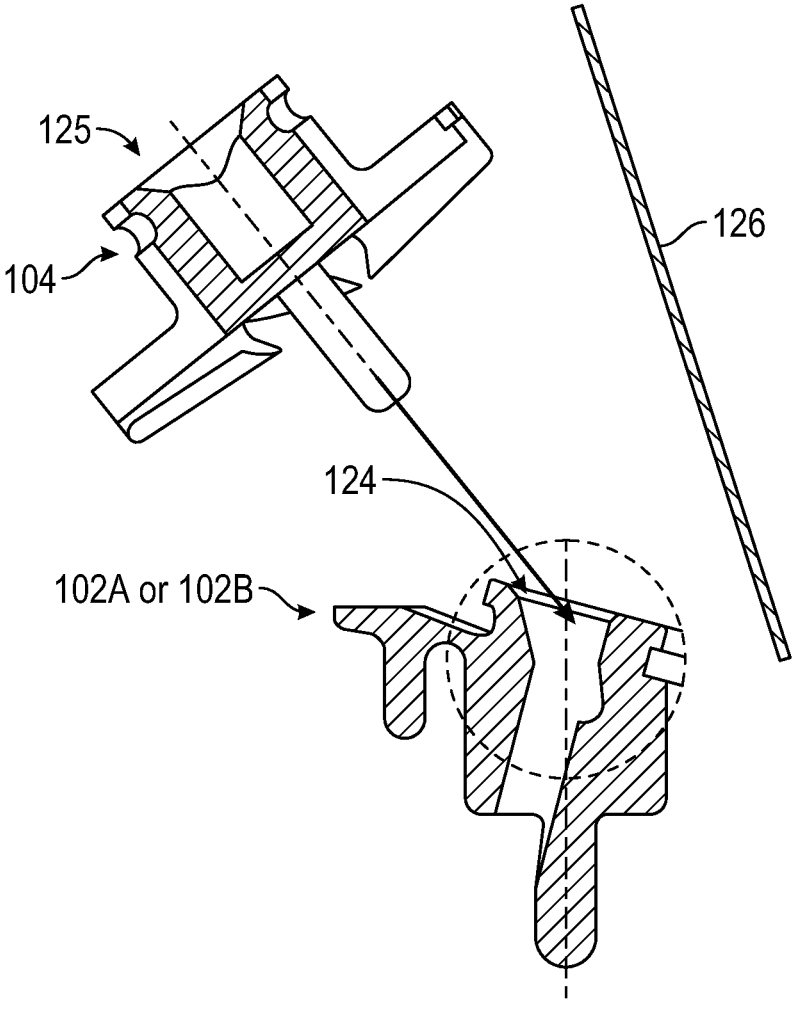
FIG. 7 shows cross-sectional view of the cutting instrument and the guide of FIG. 5 or 6 with the oblong or oval shaped opening showing an approach of the cutting instrument at an angle with respect to the guide hole portion facilitated by the pilot hole portion of the aperture according to an example of the present application.

FIG. 7 shows a benefit of the oval or oblong shape for the opening 132A or 132B is that the cutting instrument 104 can have a more extreme an angle of approach toward the aperture 124 of the guide 102. This more extreme angle is compared with the angle approach in the example of FIG. 2. This more extreme angle of approach can further avoid or minimize impact such as stretching of the soft tissue 126 of the shoulder joint 125.

Figures 8A, 8B:
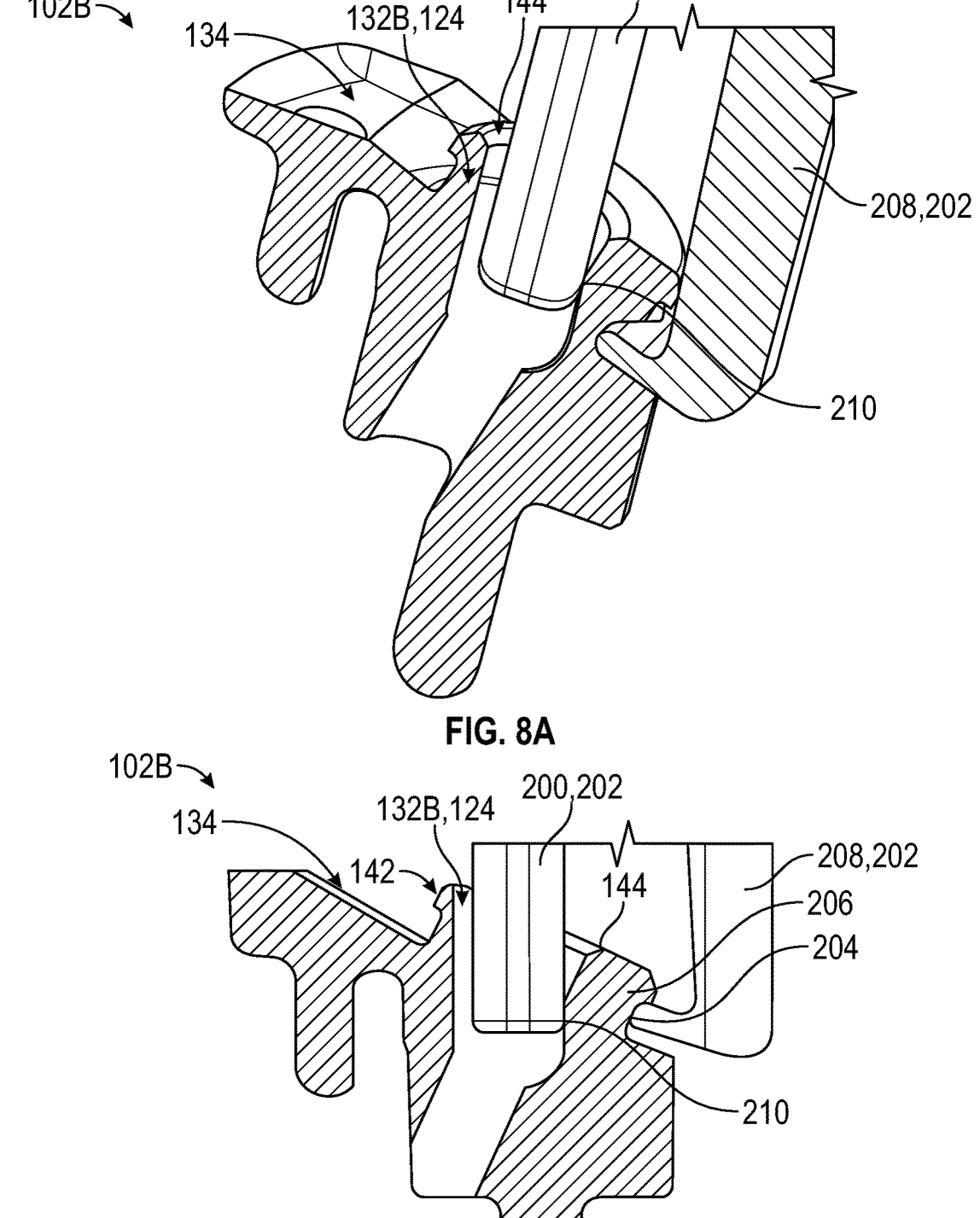
FIGS. 8A and 8B are perspective and cross-sectional views respectively of the guide of FIG. 5 or 6 being engaged by an insertion and/or removal tool according to an example of the present application.

FIGS. 8A and 8B show the guide 102B with the opening 132B at the proximal surface 144 and the aperture 124 can be configured to receive a post 200 or other suitably configured portion of an insertion/removal tool 202. The insertion/removal tool 202 can be a forceps or other suitable surgical instrument. The projection 142 (FIG. 8B) at the proximal side 134 of the guide 102B can further include a groove 204 (FIG. 8B) and lip 206 (FIG. 8B). The groove 204 (FIG. 8B) and lip 206 (FIG. 8B) can be configured to be engaged by a second portion 208 of the insertion/removal tool 202 such as a tine, prong, jaw or the like.

As shown in FIGS. 8A and 8B, an engagement surface 210 that forms part of the aperture 124 can be abutted by the post 200 during insertion and/or removal of the guide 102B in addition to engagement of the groove 204 (FIG. 8B) and lip 206 (FIG. 8B) by the second portion 208. The oval or oblong shape of the opening 132B can better facilitate engagement of the engagement surface 210 by the post 200.

Figure 8C:
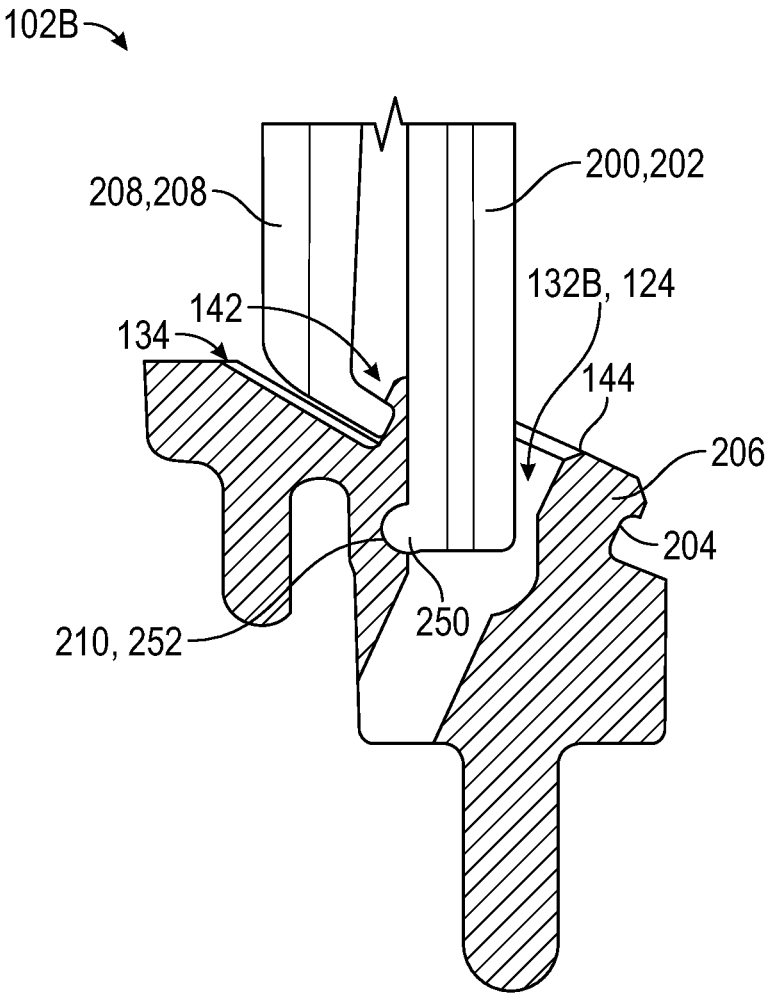
FIG. 8C shows a cross-sectional view of another example of the guide engaged by another example of the insertion and/or removal tool according to an example of the present application.

As shown in FIG. 8C, an improved engagement between post 200 and aperture 124 may be achieved by a spherical bump 250 (or other similar tip male feature such as rounded rectangle, chamfered cylinder or rounded square shape) on the end of post 200. The bump 250 can be on a medial side of the post 200 of the insertion/removal tool 202. This feature along with the second portion 208 being on the medial side of the guide 102B allows for a more medialized approach the insertion/removal tool 202 that can better avoid the soft tissue that can interfere with the second portion 208 engaging the groove 204. A similar spherical recess 252 (or other similar female recess feature such as rounded rectangle chamfered cylinder or rounded square shape) within aperture 124 on the medial side thereof (to receive the spherical bump on end of post 200) would facilitate this approach. Engagement of this spherical bump 250 (or similar male feature as described) within the accompanying spherical recess 252 (or similar female feature as described) would further improve the grip of the forceps onto the guide for extraction. It is noted that the insertion/removal tool 202 can have in some example the female feature while the guide 102B can have a corresponding male feature within aperture 124.

Figure 9:
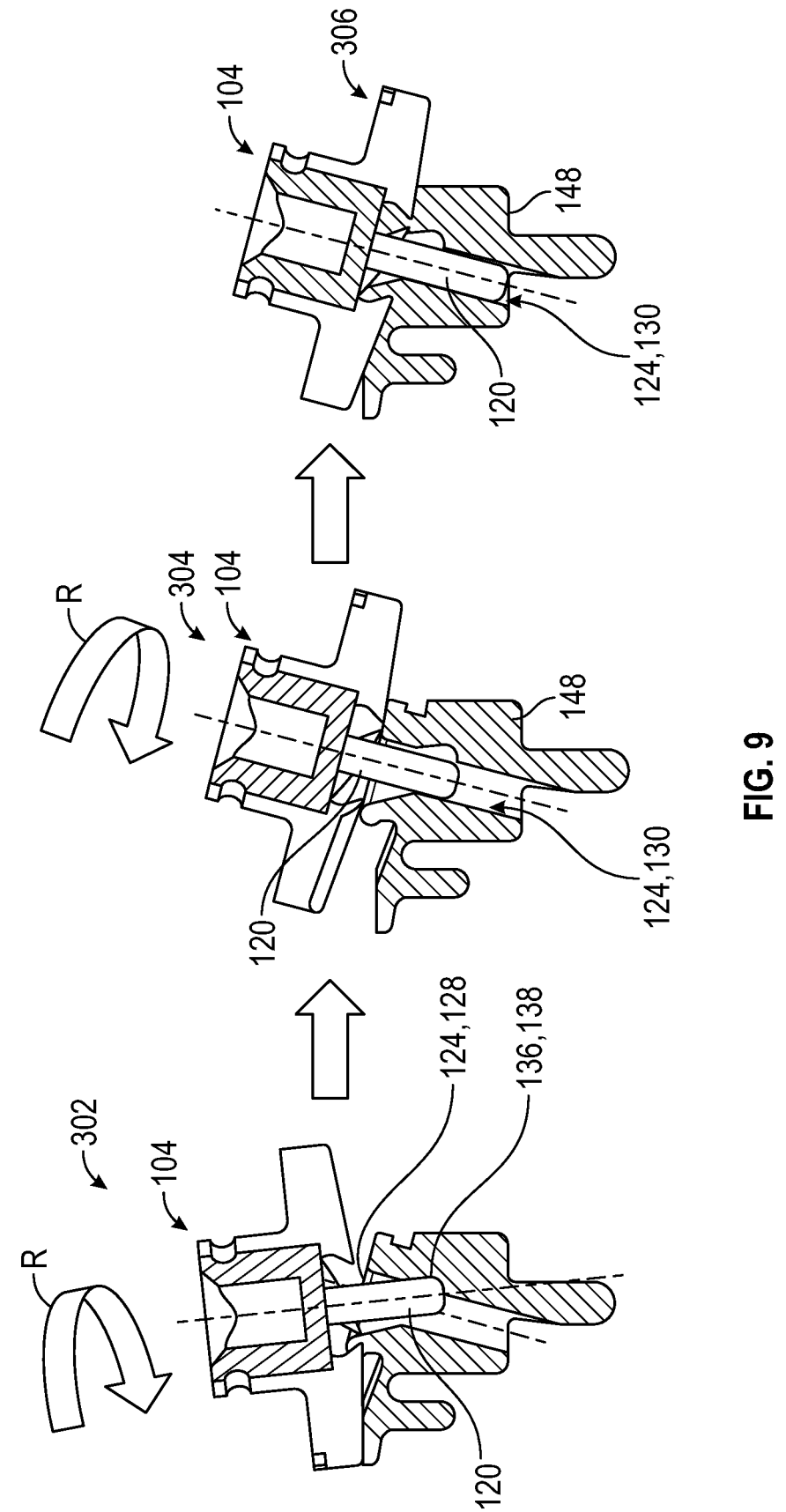
FIG. 9 shows a process whereby the cutting instrument of FIGS. 1 and 2 is initially inserted into the pilot hole portion of the aperture of the guide and then reoriented via rotational torque to be further inserted into the guide hole portion of the aperture according to an example of the present application.

FIG. 9 shows a surgical method 300 whereby the peg 120 of the cutting instrument 104 is initially partially inserted at step 302 into the pilot hole portion 128 of the aperture 124 of the guide 102 and then the peg 120 and instrument 104 is reoriented at step 304 and then the peg 120 is further inserted at step 306 into the guide hole portion 130 of the aperture 124. This method 300 can be facilitated by the shape of the one or more surfaces 136 (having radii 138) and/or can be further assisted by the shape of the tip of the peg 120, for example. Furthermore, the method 300 contemplates that the reorientation of the cutting instrument 104 from the position of step 302 to the position of step 304 can be facilitated by rotating (as indicated by arrow R) the cutting instrument 104. Such rotation could be carried out by hand or could be performed by powered (driven) rotation of the cutting instrument 104 such as using the reamer (FIG. 1), for example.

More particular, the step 302 shows the peg 120 with the tip in contact with the one or more surfaces 136 after initial partial insertion of the peg 120 into the pilot hole portion 128. Rotation of the cutting instrument 104 can continue to step 304 to the reoriented position shown. This reoriented position can allow further insertion of the peg 120 into the guide hole portion 130 toward the distal side 148 of the guide 102. The final position of step 306 shows the further insertion of the cutting instrument 104 with peg 120 positioned adjacent the distal side 148.

Figure 10:
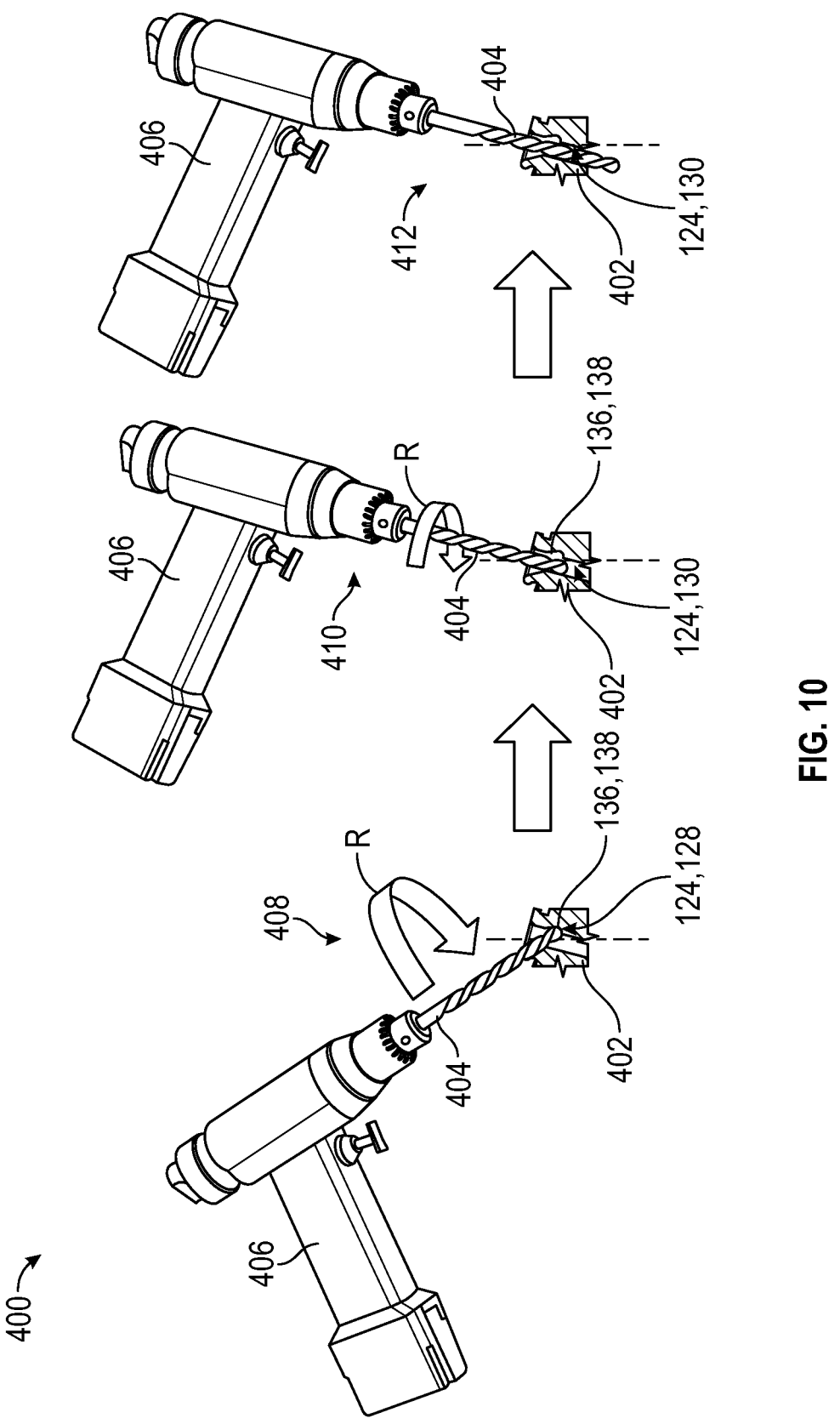
FIG. 10 shows a process whereby another example of a cutting instrument, a drill, is initially inserted into the pilot hole portion of the aperture of a guide and then reoriented via rotational torque to be further inserted into the guide hole portion of the aperture according to an example of the present application.

FIG. 10 shows a surgical method 400 similar to the method 300 of FIG. 9. The method 400 is performed with a guide 402 such as one for trauma surgery or other orthopedic repair. Thus, the guide 402 can differ in shape from the guides previously shown and discussed herein. However, the guide 402 can include the aperture 124 of similar configuration to that previously described including the pilot hole portion and the guide hole portion.

As shown in FIG. 10 a drill bit 404 of a drill 406 is utilized. The drill bit 404 (e.g., a cutting instrument) of the drill 406 is initially partially inserted at step 408 into the pilot hole portion 128 of the aperture 124 of the guide 402 and then reoriented at step 410 and then further inserted at step 412 into the guide hole portion 130 of the aperture 124. This method 400 can be facilitated by the shape of the one or more surfaces 136 (having radii 138) and can be further assisted by the shape of a tip of the drill bit 404, for example. Furthermore, the method 400 contemplates that the reorientation of the drill bit 404 from the position of step 408 to the position of step 410 can be facilitated by rotating (as indicated by arrow R) the drill bit 404. Such rotation could be carried out by hand or could be performed by powered rotation of the drill bit 404 such as by operation of the drill 406, for example.

As an example, the guide 402 can be used in other areas of orthopedics. In one example, the guide 402 can facilitate wrapping a suture or cable around or within a bone, while avoiding stretching adjacent tissues. The drill 406 (or reamer with post) can have a cannulation. This can be used for a secondary suture or cable to be introduced later through the cannula. Such a configuration would use a methodology in a similar manner to the method 400 of FIG. 10. The guide 402 can allow the drill bit 404 or other cutting instrument to go around a long bone or through a bone. The approach angle of the drill bit 404 (or other cutting instrument) can be increased (as was discussed in the glenoid example of FIGS. 1-8). This can spare surrounding soft tissues from excessive stretching during the procedure. The drill bit 404 can insert into the guide 402, contacting a spherical or tilted/angled surface and/or feature at the end/side of the pilot hole portion 128 (example illustrated in FIG. 10). Finally, the drill bit 404 would be reoriented and exit the side of the guide 402 (as shown in step 412). After this exit from the guide 402, a cable or suture could be passed through the guide 402 and/or a cannulation in the drill bit 404, in order to get around a long bone or through the bone with aid of the guide 402. In this manner, bones/tissues could be sutured or cabled around a corner at a greater approach angle, sparing adjacent tissues trauma from over-stretching them during the procedure. This may have many applications including allowing for cannulated, minimally invasive suture or cable passing instruments to get into or around a bone.

Additionally, the cutting instrument such as a cannulated drill/reamer post, etc. can be introduced in a non-rotating manner into the pilot hole portion 128 and then the application of a torque onto a shaft of the cutting instrument can assist in driving the cutting instrument tip down into the guide hole portion 130. It is contemplated by using the centrifugal force generated by rotation (such as powered rotation from the drill 406), the cutting instrument (e.g., the drill bit 404) can rotate against the one or more surfaces 136 of the pilot hole portion 128 in the guide 402. As was previously discussed, an opening with an oblong or oval shape may further allow the user to approach the guide at a greater angle. A customized approach angle could be developed to the patient's bone involved. The twist/rotation/centrifugal drop (into the guide hole portion 130 from the pilot hole portion 128) can allow the design of the tip of the cutting instrument and the pilot hole end to be optimized, within parameters of tip geometry (such as surface finish on tip, behavior of different raw materials, different tip geometries: trocar tip, conical with pointed tip, conical with rounded tip, flat tip with no edge blend and/or flat tip with different radius blends) and parameters of guide geometry (such as surface finish on the angled or spherical pilot hole bottom, behavior of different raw materials, different pilot hole bottom geometries, such as spherical or titled/angled bottom. The above optimization principles are also applicable to the glenoid example of FIGS. 1-8.

The term "proximal" refers to the general orientation of the side and/or surface when the guide is implanted in the bone or when the cutting instrument is utilized to cut tissue. Thus, "proximal" refers to a direction or location generally in the direction of or toward the head of a patient, and "distal" refers to the opposite direction of proximal, i.e., away from the head of a patient. As used herein, the terms "anterior" and "posterior" should be given their generally understood anatomical interpretation. Thus, "posterior" refers to a location or direction generally toward a rear of the patient. Similarly, "anterior" refers to a location or direction generally toward a front of the patient. Thus, "posterior" refers to the opposite direction of "anterior." Similarly, the terms "medial" and "lateral" should be given their generally understood anatomical interpretation. "Medial" refers to the more inward facing (inner part) of the guide or instrument (when in the implanted orientation) and "lateral" refers to the outer part or outward facing part. "Medial" refers to the opposite direction of "lateral."

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims. For example, the order of method steps or stages can be altered from that described above, as would be appreciated by a person of skill in the art.

It will also be appreciated that the various dependent claims, examples, and the features set forth therein can be combined in different ways than presented above and/or in the initial claims. For instance, any feature(s) from the above examples can be shared with others of the described examples, and/or a feature(s) from a particular dependent claim may be shared with another dependent or independent claim, in combinations that would be understood by a person of skill in the art.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for performing an orthopedic surgical procedure, the system comprising:

a cutting instrument configured to cut a bone of a patient with one or more cutting features, wherein the cutting instrument includes a peg distal of the one or more cutting features, wherein the cutting features extend radially outward of peg;

a guide configured to mount to the bone, the guide defining an aperture having a guide hole portion and a pilot hole portion, wherein the pilot hole portion is configured to initially receive a portion of the bone cutting instrument, and wherein an axis of the pilot hole portion is oriented at an acute angle relative to an axis of the guide hole portion, wherein the guide has one or more reorientation surfaces that form the aperture, wherein the one or more reorientation surfaces form one or more of a side and bottom of the pilot hole portion, and wherein the one or more reorientation surfaces include a radius of curvature;

wherein the peg is the portion of the bone cutting instrument initially received by the pilot hole portion, and wherein the peg has a blunt tip configured to engage the one or more reorientation surfaces; and wherein the cutting instrument is rotatable within the pilot hole portion of the aperture and rotation of the cutting instrument contacts the peg with the one or more reorientation surfaces to reposition the peg to be received in the guide hole portion;

wherein the cutting instrument is rotatable in the guide hole portion to cut the bone of the patient with the one or more cutting features.

2. The system of claim 1, wherein the one or more reorientation surfaces form a partial spherical shape.

3. The system of claim 1, wherein the guide includes a proximal surface and the aperture communicates with the proximal surface at an opening, and wherein the opening in cross-section is one of oval, oblong or compound curved.

4. The system of claim 1, further comprising an instrument configured to insert and/or remove the guide, wherein the guide includes a groove configured to be engaged by a prong of the instrument, and wherein the instrument includes a projection configured to insert into the aperture and engage a side surface of the aperture.

5. The system of claim 1, wherein the guide hole portion comprises a thru hole that extends to communicate with a distal surface of the guide.

\* \* \* \* \*